United States Patent [19]

Prasad

[11] Patent Number: 4,619,810
[45] Date of Patent: Oct. 28, 1986

[54] DENTAL ALLOYS FOR PORCELAIN-FUSED-TO-METAL RESTORATIONS

[75] Inventor: Arun Prasad, Cheshire, Conn.

[73] Assignee: Jeneric Industries, Inc., Wallingford, Conn.

[21] Appl. No.: 783,327

[22] Filed: Oct. 3, 1985

Related U.S. Application Data

[63] Continuation of Ser. No. 570,627, Jan. 13, 1984, abandoned.

[51] Int. Cl.$^4$ ............................................. C22C 5/04
[52] U.S. Cl. ................................... 420/463; 433/207
[58] Field of Search ............... 420/463, 465, 464, 587, 420/580; 433/200, 207

[56] References Cited

U.S. PATENT DOCUMENTS

| | | | |
|---|---|---|---|
| 3,819,366 | 6/1974 | Katz | 420/463 |
| 4,021,577 | 5/1980 | Ingersoll et al. | 420/587 |
| 4,419,325 | 12/1983 | Prasad | 420/587 |
| 4,539,176 | 9/1985 | Cascone | 420/463 |

Primary Examiner—L. Dewayne Rutledge
Assistant Examiner—S. Kastler
Attorney, Agent, or Firm—Kramer and Brufsky

[57] ABSTRACT

Palladium based dental alloys are provided consisting essentially of, on a weight percent basis:
  Gold: 8–25
  Gallium: 0–10
  Boron: 0.05–0.25
  Rhenium: 0.1–0.5
  Indium and/or Tin: 0–20
  Zinc: 0–4 and the balance, palladium—with the proviso that when a mixture of gallium, indium and/or tin are incorporated in the alloy, if gallium is present in amounts less than or equal to about 4% by weight, then the total weight percent of gallium, indium and/or tin ranges from about 12 to 20; whereas, if gallium is present in amounts from greater than about 4% to 10% by weight, then the total weight percent of gallium, indium and/or tin ranges from about 8 to 20; and when a mixture of zinc, indium and/or tin are incorporated in the alloy, zinc is present in an amount less than 4% and is present in the alloy in lieu of gallium, said alloy exhibiting a yield strength greater than 50,000 psi, an ultimate tensile strength of greater than 60,000 psi, an elongation greater than 10%, and a melting point ranging from 2200°–2400° F.

Essentially bubble-free, porcelain-fused-to-metal dental restorations are also provided comprising porcelain fired to such palladium based dental alloys.

9 Claims, No Drawings

DENTAL ALLOYS FOR PORCELAIN-FUSED-TO-METAL RESTORATIONS

This application is a continuation of application Ser. No. 570,627 filed Jan. 13, 1984, now abandoned.

This invention relates to palladium based dental alloys and, in particular, to alloys for use in porcelain-fused-to-metal restorations.

Porcelain-fused-to-metal restorations consist of a metallic sub-structure coated with a veneer of porcelain. Over the years, various alloys have been proposed for the sub-structure of such restorations. Many of the early alloys used gold with some platinum or palladium as the main alloy ingredients. Thus, for example, U.S. Pat. No. 4,123,262 describes a silverless gold alloy consisting, on a weight basis, of about 50 to 58% gold, 0.5 to 10.5% indium, 0.5 to 8.5% tin, or 1.0 to 3.0% gallium, and the balance, palladium. Similarly, U.S. Pat. No. 4,205,982 describes a gold alloy consisting essentially of about 45 to 60% gold, 30 to 50% palladium, 2 to 7% tin, 3 to 10% of zinc, indium or mixtures thereof and 0 to 2% of rhenium, nickel, platinum or mixtures thereof as a grain refining component.

With the increases and fluctuations in the price of gold and platinum in recent years, extensive efforts have been made to substantially reduce the gold content of such alloys (see, for example, U.S. Pat. No. 4,179,288). While there is obviously an economic benefit realized when using less gold, such economic benefit is often achieved at the expense of the physical properties of the alloy. In addition, many attempts have been made to substitute silver, nickel, cobalt, copper and other elements substantially less expensive than gold in such alloys. These substitutions, however, have given rise to a whole host of new problems, e.g., silver discolors the porcelain fired thereon; nickel is considered by some to be an allergen in the oral cavity; and cobalt and copper have been found to give rise to darker than desirable oxides.

Thus, the high gold content alloys are still the standard by which comparisons are made.

It is therefore an object of the present invention to provide an economical palladium-gold alloy which has all the economic advantages of a low gold alloy with physical properties comparable to the high gold alloys.

It is another object of the present invention to provide an economical palladium-gold alloy exhibiting thermal properties which are superior to high gold alloys giving rise to the use thereof with a wider range of commercial porcelains than can be employed with high gold alloys.

It is still another object to provide an economical palladium-gold alloy which is free of silver, nickel, copper and cobalt.

It is a still further object to provide an economical palladium-gold alloy which is higher melting and exhibits a higher modulus of rigidity thereby providing better marginal integrity and adaptability than the high gold alloys.

It is yet another object to provide an economical palladium-gold alloy which exhibits excellent grain structure and is not susceptible to hot tearing during the investment casting process.

These as well as other objects and advantages are provided by the palladium based dental alloy of the present invention which consists essentially, on a weight basis, of:

Gold: 8–25%
Gallium: 0–10%
Boron: 0.05–0.25%
Rhenium: 0.1–0.5%
Indium and/or Tin: 0–20%
Zinc: 0–4% and the balance, palladium—with the proviso that when a mixture of gallium, indium and/or tin are incorporated in the alloy, if gallium is present in amounts less than or equal to about 4% by weight, then the total weight percent of gallium, indium and/or tin ranges from about 12 to 20; whereas, if gallium is present in amounts from greater than about 4% to 10% by weight, than the total weight percent of gallium, indium and/or tin ranges from about 8 to 20, and when a mixture of zinc, indium and/or tin are incorporated in the alloy, zinc is present in an amount less than 4% and is present in lieu of gallium, said alloy exhibiting a yield strength greater than 50,000 psi., an ultimate tensile strength of greater than 60,000 psi, an elongation greater than 10%, and a melting point ranging from 2200°–2400° F.

Surprisingly, it has been found that by incorporating from about 8-25% of gold in the alloy, the economic benefits obtained by a rather substantial reduction in gold content can be achieved without sacrificing the physical properties as occurs when the gold content is reduced below about 5%.

While the use of gallium is optional, it is considered preferable to employ gallium in amounts ranging from about 4 to 10% since it is very effective in lowering the melting point of palladium and also assists in the attainment of physical properties comparable to higher gold alloys. If desired, indium, tin, or a mixture of indium and tin can be used to replace gallium; however, neither indium nor tin are as effective as gallium in reducing the melting point of palladium. Therefore, up to about 20% of indium or tin or mixtures thereof must be employed in lieu of gallium. Preferably, when indium and/or tin are employed, they are employed in amounts ranging from about 15–20% by weight. If desired, a mixture of gallium, indium and tin can be employed. In such instances, if gallium is present in amounts less than or equal to about 4% by weight, than the total weight percent of gallium, indium and/or tin ranges from about 12 to 20; whereas, if gallium is present in amounts greater than about 4% to 10% by weight, then the total weight percent of gallium, indium and/or tin ranges from about 8 to 20. It has also been found that comparable results can be achieved if zinc is used in lieu of gallium in combination with indium and tin; however, less than about 4% zinc is employed in such mixtures. Care should be taken to ensure that zinc and gallium are not used together, otherwise the resulting alloy will be prone to formation of a low melting phase during porcelain application. The use of these additives is effective to reduce the melting point of the resulting alloy to 2200°–2400° F. and to adjust the physical and thermal properties of the alloys. In addition, these additives provide an adherent oxide which is responsible for chemical bonding in a porcelain-fused-to-metal composite.

Boron is added to the alloy in amounts ranging from about 0.05 to 0.25% and preferably in an amount ranging from 0.05 to 0.1% to serve as a scavenger for oxygen absorbed by the alloy during the melting and casting processes. Use of boron in an amount in excess of 0.25% renders the alloy too brittle for dental applications.

From about 0.1 to 0.5% of rhenium is employed to grain refine the alloy. Alloys consist of individual grains in contact with each other. The size of the grains is critical to the physical properties of the alloy. This size can vary from coarse to fine, and the grains can be regular or irregular. Ideally, a fine, equi-axed grain structure is achieved through grain refining. Alloys with this type of grain structure exhibit superior elongation, tensile strength and toughness properties. Moreover, such alloys are less prone to hot tearing during the investment casting process, as compared to alloys with a coarser grain structure. "Hot tearing", as understood in the art, involves the formation of cracks in the casting due to stresses produced in the casting as it cools in the investment. These cracks can result in fractures which necessitate remaking the casting with the concomitant loss of the time, energy and material used to make the original casting.

If desired, up to about 2% of the noble metals, i.e., palladium and gold, can be replaced by any of the other noble metals such as platinum, iridium or ruthenium.

Preferably, the alloy consists essentially of gold—15%, palladium—76.65%, gallium—8%, boron—0.05%, and rhenium—0.3%.

The grain-refined alloys of the present invention should not be prepared in air, the standard technique, because to do so leads to the formation of bubbles in the porcelain during the porcelain firing process. Rather, the grain-refined alloys must be formed in a protective environment, such as, under vacuum, in a reducing atmosphere or in an inert atmosphere, for example, an atmosphere of argon. Without proceeding in this manner, the alloy absorbs gases from the atmosphere which are later released from the alloy during firing to form bubbles in the porcelain. Also, it has been found that carbon containing crucibles are not advantageous in the preparation of the alloys of the present invention. Rather, ceramic crucibles, e.g., zirconia crucibles, are preferred.

When argon is used as the protective environment, it is preferrably introduced after vacuum has been applied to the melting chamber to remove ambient air. Alternatively, a stream of argon can be passed through the chamber without first drawing a vacuum. When only a vacuum is used, the temperature of the melt and the applied vacuum must be controlled in view of the vapor pressures of the components of the alloy to avoid excessive relative losses of the more volatile components. In particular, when zinc is included in the alloy, a protective environment comprising a reducing or an inert gas, rather than a vacuum environment, should be used in forming the alloy in view of the relatively high vapor pressure of zinc.

The following Table further illustrates two alternative embodiments of the present invention. These specific alloys are not to be construed as in any way limiting the scope of this invention. All percentages and parts are by weight. Each of the following alloys exhibited a fine, equi-axed grain refined structure.

For comparative purposes, a typical high gold alloy consisting of Au—50.75%, Pd—40.0%, In—7.5% and Ga—1.75% exhibited the following properties: Yield strength—72,000 psi; ultimate tensile strength—102,000 psi; and elongation—24%.

TABLE

| Alloy No. | Alloy Elements | | | | | Properties[1] | | |
|---|---|---|---|---|---|---|---|---|
| | Pd | Au | Ga | B | Re | Yield Strength (psi) | Ultimate Tensile Strength (psi) | Elongation (%) |
| 1 | 81.65 | 10 | 8 | 0.05 | 0.3 | 65,000 | 90,000 | 24 |
| 2 | 76.65 | 15 | 8 | 0.05 | 0.3 | 80,000 | 100,000 | 25 |

[1]Properties were determined after a simulated procelain firing cycle comprising placing the alloy at room temperature into a furnace maintained at 1200° F. and heating at the rate of 100° F./minute until the alloy reached 1850° F., then allowing the alloy to cool to room temperature and then repeating the heating and cooling cycle a total of five times.

What is claimed is:

1. A palladium based dental alloy, free of silver, nickel, copper and cobalt, consisting essentially of, on a weight percent basis:
   gold, 8-25
   gallium, 4-10
   boron, 0.05-0.25
   rhenium, 0.1-0.5
   indium and/or tin, 0-20
and the balance, palladium—with the proviso that when a mixture of gallium, indium and/or tin is incorporated in the alloy, the total weight percent of gallium, indium and/or tin ranges from about 8 to 20, said alloy exhibiting a yield strength greater than 50,000 psi, an ultimate tensile strength of greater than 60,000 psi, an elongation greater than 10%, and a melting point ranging from 2200° to 2400° F.

2. A palladium based dental alloy as defined in claim 1 wherein boron is present in the alloy in an amount ranging from about 0.05 to 0.1 percent by weight.

3. A palladium based dental alloy consisting essentially of, on a weight percent basis, gold—10%, palladium—81.65%, gallium—8%, boron—0.05%, and rhenium—0.3%.

4. A palladium based dental alloy consisting essentially of, on a weight percent basis, gold—15%, palladium—76.65%, gallium—8%, boron—0.05%, and rhenium—0.3%.

5. A palladium based dental alloy as defined in claim 1 wherein up to about 2% of palladium and/or gold is replaced by platinum, iridium or ruthenium.

6. An essentially bubble-free, porcelain-fused-to-metal dental restoration comprising porcelain fused to a palladium based dental alloy as defined in claim 1.

7. An essentially bubble-free, porcelain-fused-to-metal dental restoration comprising porcelain fused to a palladium based dental alloy as defined in claim 3.

8. An essentially bubble-free, porcelain-fused-to-metal dental restoration comprising porcelain fused to a palladium based dental alloy as defined in claim 4.

9. An essentially bubble-free, porcelain-fused-to-metal dental restoration comprising porcelain fused to a palladium based dental alloy as defined in claim 5.

* * * * *